United States Patent
Takeshige et al.

(10) Patent No.: US 6,778,208 B2
(45) Date of Patent: Aug. 17, 2004

(54) ELECTRONIC ENDOSCOPE SYSTEM

(75) Inventors: Masaru Takeshige, Tokyo (JP); Hiroyuki Kobayashi, Saitama (JP)

(73) Assignee: PENTAX Corporation, Tokyo (JP)

(*) Notice: Subject to any disclaimer, the term of this patent is extended or adjusted under 35 U.S.C. 154(b) by 28 days.

(21) Appl. No.: 09/990,302

(22) Filed: Nov. 23, 2001

(65) Prior Publication Data

US 2002/0085091 A1 Jul. 4, 2002

(30) Foreign Application Priority Data

Dec. 28, 2000 (JP) ........................... P2000-400694

(51) Int. Cl.[7] ............................ H04N 7/18; H04N 9/47; A62B 1/04
(52) U.S. Cl. ........................ 348/65; 348/159; 348/71; 348/74
(58) Field of Search ................. 348/65, 159, 71, 348/74; 606/1

(56) References Cited

U.S. PATENT DOCUMENTS

| 5,776,050 A | * | 7/1998 | Chen et al. ............... 600/117 |
| 5,788,688 A | * | 8/1998 | Bauer et al. ............... 606/1 |
| 6,174,291 B1 | * | 1/2001 | McMahon et al. ......... 600/564 |
| 6,215,517 B1 | * | 4/2001 | Takahashi et al. ......... 348/72 |
| 6,476,852 B1 | * | 11/2002 | Okada ....................... 348/65 |
| 6,538,687 B1 | * | 3/2003 | Saito et al. ................. 348/65 |
| 6,563,596 B1 | * | 5/2003 | Narushima ................ 358/1.14 |

OTHER PUBLICATIONS

Exerpts from "Windows 95 for Dummies" Andy Rathbone, pp. 32, 189, 88, copyright 1997, IDG books.*
Andy Rathbone, Windows For Dummies, IDG books, copyright 1995 pp. 32, 188 and 189.*

* cited by examiner

Primary Examiner—Chris Kelley
Assistant Examiner—Charles E Parsons
(74) Attorney, Agent, or Firm—Greenblum & Bernstein, P.L.C.

(57) ABSTRACT

An electronic endoscope system is provided with an outputting device specifying tool and a database having tables. In the tables, compensation data, for compensating image signals generated by the system in accordance with outputting devices, are recorded. When the model of outputting device is specified by the specifying tool, the tables are searched using the name of the specified model of outputting device as a search key, so that compensation data for compensating the image signals in accordance with the characteristics of the connected outputting device can be obtained. The image signals are output to the connected outputting device, after being compensated based on the compensation data.

12 Claims, 12 Drawing Sheets

FIG. 3

```
RGB OUTPUT 1 SET

MONITOR A      VCR A
* MONITOR B      VCR B
  MONITOR C      VCR C
  PRINTER A
  PRINTER B
  PRINTER C
```

```
S-Video OUTPUT 1 SET

MONITOR A      VCR A
  MONITOR B      VCR B
  MONITOR C      VCR C
* PRINTER A
  PRINTER B
  PRINTER C
```

```
Y/C OUTPUT 1 SET

MONITOR A      VCR A
  MONITOR B      VCR B
  MONITOR C    * VCR C
  PRINTER A
  PRINTER B
  PRINTER C
```

FIG. 4

| | STANDARD | MONITOR A | MONITOR B | | | MONITOR C |
|---|---|---|---|---|---|---|
| | R,G,B | R,G,B | R | G | B | R,G,B |
| $\alpha$ | 1 | 1 | 2 | 1 | 1 | 0.5 |

FIG. 5

| | STANDARD | MONITOR A | MONITOR B | | | MONITOR C |
|---|---|---|---|---|---|---|
| | R,G,B | R,G,B | R | G | B | R,G,B |
| COLOR BALANCE | 0 | 0 | +2 | −1 | 1 | −2 |

FIG. 6

| INPUT | OUTPUT | | | | | | |
|---|---|---|---|---|---|---|---|
| | STANDARD | MONITOR A | MONITOR B | | | MONITOR C | |
| | R,G,B | R,G,B | R | G | B | R,G,B | |
| 0 | 8 | 10 | 11 | 10 | 11 | 7 | |
| 10 | 36 | 38 | 40 | 38 | 40 | 34 | |
| 20 | 49 | 52 | 55 | 52 | 55 | 48 | |
| 30 | 58 | 59 | 62 | 59 | 62 | 57 | |
| 40 | 66 | 67 | 69 | 67 | 69 | 65 | |
| 50 | 73 | 74 | 75 | 74 | 75 | 72 | |
| 60 | 79 | 80 | 81 | 80 | 81 | 78 | |
| 70 | 85 | 85 | 86 | 85 | 86 | 85 | |
| 80 | 90 | 90 | 91 | 90 | 91 | 90 | |
| 90 | 95 | 95 | 95 | 95 | 95 | 95 | |
| 100 | 100 | 100 | 100 | 100 | 100 | 100 | |

(EACH VALUE INDICATES PERCENTAGE (%) OF MAXIMUM)

FIG. 8

| INPUT | OUTPUT | | | | | |
|---|---|---|---|---|---|---|
| | STANDARD | MONITOR A | MONITOR B | | | MONITOR C |
| | R,G,B | R,G,B | R | G | B | R,G,B |
| 0 | 0 | 30 | 20 | 30 | 0 | 10 |
| 10 | 10 | 37 | 28 | 37 | 10 | 19 |
| 20 | 20 | 44 | 36 | 44 | 20 | 28 |
| 30 | 30 | 51 | 44 | 51 | 30 | 37 |
| 40 | 40 | 58 | 52 | 58 | 40 | 46 |
| 50 | 50 | 65 | 60 | 65 | 50 | 55 |
| 60 | 60 | 72 | 68 | 72 | 60 | 64 |
| 70 | 70 | 79 | 76 | 79 | 70 | 73 |
| 80 | 80 | 86 | 84 | 86 | 80 | 82 |
| 90 | 90 | 93 | 92 | 93 | 90 | 91 |
| 100 | 100 | 100 | 100 | 100 | 100 | 100 |

(EACH VALUE INDICATES PERCENTAGE (%) OF MAXIMUM)

ELECTRONIC ENDOSCOPE SYSTEM

BACKGROUND OF THE INVENTION

1. Field of the Invention

This invention relates to an electronic endoscope system in which image data, which are obtained by an electronic scope, are subjected to predetermined operations and the image data are reproduced by an outputting device.

2. Description of the Related Art

Conventionally, a medical examination using an electronic endoscope system is performed as follows. An electronic scope is inserted into the digestive organ, and image signals are obtained by an image sensor which is provided at a tip end portion of the electronic endoscope. The image signals are subjected to predetermined image processing in an image-signal processing unit to which the electronic scope is connected. The processed image signals are output to an outputting device, for example a monitor and a printer, from the image-signal processing unit. An operator manipulates the electronic rope, viewing pictures of the inside of the digestive organ which are reproduced on the monitor. Further, if necessary, still pictures of lesion portions reproduced on the monitor are output to the printer.

In the medical examination described above, the operator judges the condition of a patient by viewing the color of the inner wall of digestive organ, and judges whether a lesion has occurred or not. Accordingly, in the electronic endoscope system, it is required that the picture reproduced by the outputting device has stability regarding color.

However, the hue and brightness of the picture reproduced on the monitor and on the printing sheet depend upon the characteristics of type of monitor and printer which are connected to the image-signal processing unit. Namely, even if identical image signals are output from identical image-signal processing units, the color condition of a reproduced image differs in accordance with the type of outputting device. Namely, with respect to picture quality, differences according to the type of outputting device exist.

Accordingly, it is necessary for the operator to adjust the picture quality of the reproduced image in accordance with the characteristics of the outputting device which is connected to the image-signal processing unit. It is complicated to carry out the above-mentioned adjustment while manipulating the electric scope in the body of a patient. Namely, the adjustment of the outputting device imposes a burden on the operator. Further, if the adjustment is not carried out, the colors of images obtained by the image sensor are not able to be accurately reproduced by the outputting device, so that lesion portions may be missed by the operator.

SUMMARY OF THE INVENTION

Therefore, an object of the present invention is to provide an image-signal processing unit which can function well with various outputting devices.

In accordance with an aspect of the present invention, there is provided an electronic endoscope system, provided with an image-signal processing unit that processes image signals obtained by a scope which is connected to the image-signal processing unit attachably and detachably, and at least one outputting device that is connected to the image-signal processing unit in order to output the image signals. The electronic endoscope system comprises: an outputting device specifying tool that specifies the model of the at least one outputting device; a database storing characteristic data concerning the output characteristics of each model of outputting device; and an image-signal compensator that obtains the characteristic data from the database based on the model specified by the outputting device specifying tool, and compensates the image signals using the obtained characteristic data.

Preferably, the image-signal processing unit comprises a plurality of output terminals to which the outputting devices can be connected, and the model of the outputting devices is specified by the outputting device specifying tool with respect to each of the output terminals.

Preferably, the outputting device specifying tool comprises: a menu displayer that displays a list of models of the outputting devices; and an input tool that selects one of the models corresponding to the connected outputting devices, from the list. The said list is displayed corresponding to each of the output terminals.

Preferably, the outputting device specifying tool is a rotary switch that is provided for each of the output terminals.

Optionally, the database is stored in a storage medium that is able to be replaced.

Optionally, the image-signal processing unit is able to be connected to an information communication network, and the database is able to be maintained by a remote terminal unit which is connected to the information communication network.

For example, the outputting devices are a monitor and a printer on which the image signals are reproduced.

Preferably, the characteristic data are data concerning picture quality of an image which is reproduced by each outputting device.

For example, the characteristic data might include a compensation coefficient used for a contour correction process.

For example, the characteristic data might include a compensating value used for adjustment of the color balance of the image signals.

For example, the characteristic data might include an output level value used for gamma correction of the image signals.

For example, the characteristic data might include an output level value used for clamping the black level of the image signals.

According to the present invention, the image signals obtained by the scope are compensated in accordance with the characteristics of the outputting device which is connected to the image-signal processing unit. Therefore, even if an outputting device, whose picture quality characteristics are different from another, is connected to the image-signal processing unit, the same picture quality is guaranteed in reproduced image. Namely, it is not necessary for an operator to adjust the picture quality considering the characteristics of the connected outputting device during a medical examination, so that the burden of the operator can be reduced.

If the database is stored in the storage medium which is able to be replaced, the database can be readily updated in the image-signal processing unit of the electronic endoscope system by installing a new storage medium in which the updated database is stored. Namely, it is easy to maintain the database. Further, it is easy to maintain a secure database, by dealing with the storage medium carefully.

By connecting the image-signal processing unit to the information communication network such that the processing unit can be accessed by a remote terminal unit connected to the information communication network, it is possible to maintain the database at a place where the electronic endoscope system is not installed. Accordingly, the burden of having the personnel necessary for maintaining the database can be reduced.

Note that, the characteristic data are not limited to the compensation coefficients for the contour correction process, the value of the color balance, the output level value used in the gamma correction process, and the output level value used for clamping the black level.

BRIEF DESCRIPTION OF THE DRAWINGS

The objects of the present invention will be better understood from the following description, with reference to the accompanying drawings, in which:

FIG. 3 is an example of a submenu for selecting the type of outputting device;

FIG. 4 is an example of records of a compensation coefficient table used for the contour correction process;

FIG. 5 is an example of records of a color balance table used for the color balancing process;

FIG. 6 shows examples of records of a gamma correction table used for the gamma correction process;

FIG. 8 shows a table of examples of a black level settings used for clamping the black level;

DESCRIPTION OF THE PREFERRED EMBODIMENTS

Figure 1:
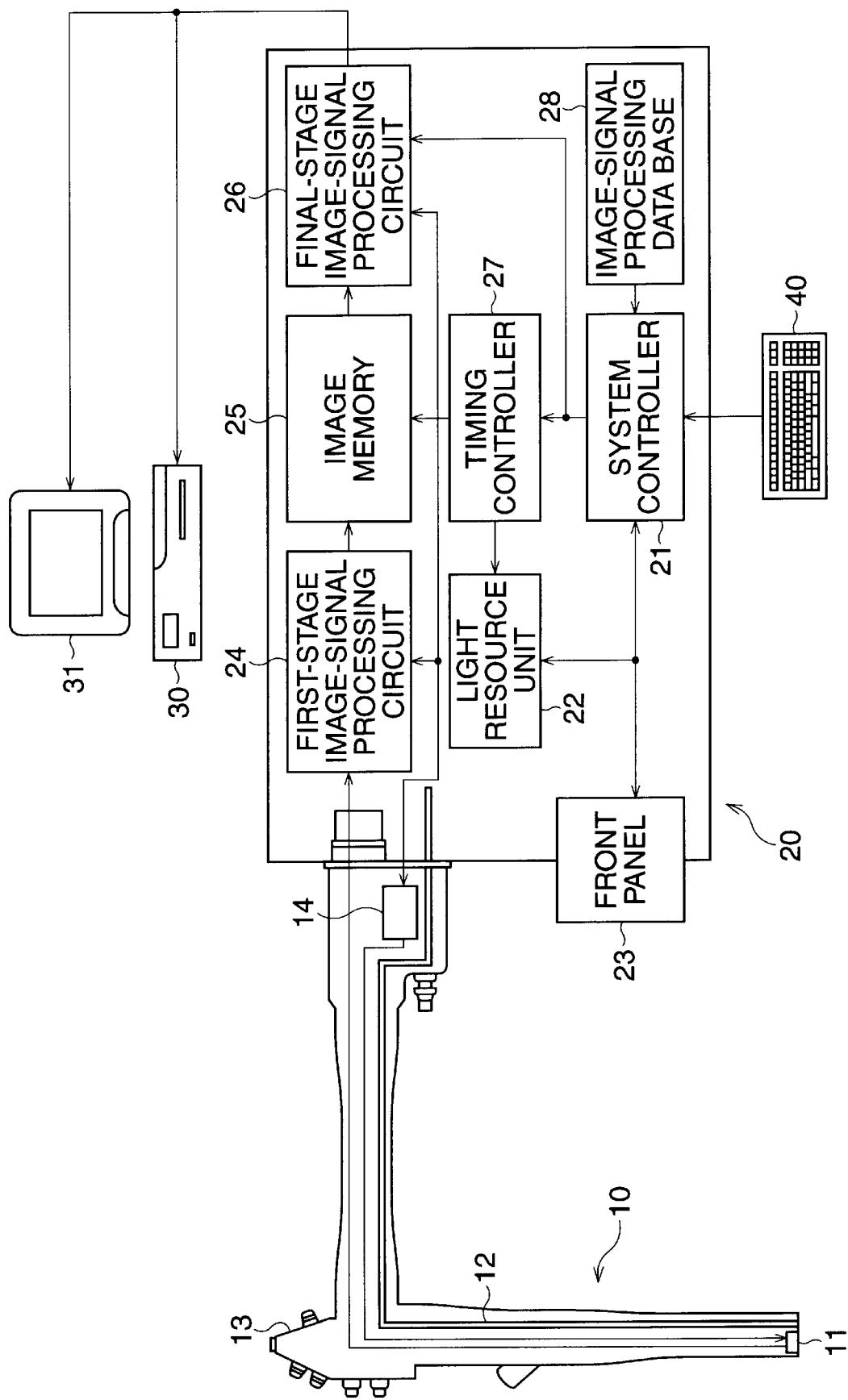
FIG. 1 is a block diagram showing an electronic endoscope system to which a first embodiment according to the present invention is applied.

FIG. 1 is a block diagram showing an electronic endoscope system to which a first embodiment according to the present invention is applied. An electronic scope 10 has a flexible tube. The electronic scope 10 is connected to an image-signal processing unit 20, in such a manner that the scope 10 is attachable to and detachable from the unit 20. An image sensor 11 is provided at the tip end of the scope 10. The image sensor 11 has an objective optical system and a CCD image sensor. A light guide 12, which is a bundle of extra fine optical fibers, is inserted in the scope 10. An emitting end of the light guide 12 is arranged at the distal end of the scope 10. A control portion 13 of the scope 10 is provided with control buttons, such as a freeze button, copy button, record button and so on. Moving pictures are stilled by manipulating the freeze button. Still pictures are stored by manipulating the record button. Namely, image signals which are processed in the image-signal processing unit 20 are recorded by manipulating the control buttons.

A system controller 21 is, for example, a micro computer, and wholly controls the electronic endoscope system. Namely, the system controller 21 has a CPU, a ROM in which programs for performing routines and invariables and so on are stored, and a RAM for storing temporary data.

When the scope 10 is connected to the image-signal processing unit 20, the CCD image sensor of the image sensor 11 is connected to a first-stage signal processing circuit 24 of the unit 20 through a CCD buffer circuit (omitted in FIG. 1). Also, another end of the light guide 12 or an incident end is optically connected with a light source unit 22 which has a white light source (omitted in FIG. 1), for example, a xenon lamp, a tungsten halogen lamp, and so on.

A diaphragm and a collective lens (omitted in FIG. 1) are situated between the incident end of the light guide 12 and the light source unit 22. The quantity of light which is incident in the incident end of the light guide 12 is controlled by the diaphragm. The light emitted from the white light source is led to the incident end of the light guide 12.

The image-signal processing unit 20 is provided with a front panel 23. The front panel 23 is provided with switches, for example, a power switch for controlling the ON/OFF status of the main power (omitted in FIG. 1) of the image-signal processing unit 20, a light switch for controlling the ON/OFF status of the light source unit 22, and so on.

The system controller 21 outputs a control signal to a lamp power circuit (omitted in FIG. 1) of the light source unit 22 based on a signal input from the light switch. Based on the control signal of the system controller 21, the electric supply to the white light source is controlled by the lamp power circuit.

Further, an RGB rotational color filter (omitted in FIG. 1) is provided at the emitting side of the white light source of the light source unit 22. The RGB rotational color filter has a red (R) colored filter, a green (G) colored filter and a blue (B) colored filter. The colored filters are supported by a circular plate member, being positioned at regular intervals on the circular plate member.

The RGB rotational color filter is rotated by a driving motor, for example, a servo motor, a stepping motor and so on. When the RGB rotational color filter is rotated while the white light source is turned on, a red colored light, a green colored light and a blue colored light are emitted in sequence from the emitting end of the light guide 12, so that a viewed subject is sequentially illuminated with the red colored light, the green colored light and the blue colored light. With respect to each color of RGB, the optical image of the viewed subject is imaged on the CCD image sensor by the objective optical system.

The image sensor 11 photoelectrically converts the optical image for each RGB color and generates analog pixel signals for one frame. The analog pixel signal for each RGB color is output from the image sensor 11 by a CCD driver 14 which is provided in the scope 10.

Under the control of the CCD driver 14, the analog pixel signal of each RGB color is read out and input to the first-stage image-signal processing circuit 24. The first-stage image-signal processing circuit 24 is provided with a preamplifier, a band-pass video filter and so on. The input analog pixel signals are subjected to predetermined signal operations, for example, amplification.

After the predetermined signal operations by the first-stage image-signal processing circuit 24, the analog pixel signals for each color are converted to digital pixel signals by an A/D converter (omitted in FIG. 1) and the digital pixel signals for each color are stored in the image memory 25. The digital pixel signal for each color is simultaneously read out from the memory 25 and input to the final-stage image processing circuit 26.

In the final-stage image processing circuit 26, the digital pixel signal for each RGB color is subjected to predetermined operations, referring to an image-signal processing database 28, and is then sent to a printer 30 and a TV monitor 31. Accordingly, the image of the viewed subject can be printed by the printer 30, being reproduced on the TV monitor 31 as a color image. Timing of the A/D conversion, storage the pixel signals in the image memory 25, generation of the synchronous signal, and so on are controlled by a timing controller 27. Note that, the predetermined operations of the final-stage image-signal processing circuit 26 will be explained next.

A keyboard 40 or a command inputting tool is connected to the image-signal processing unit 20. For example, a command for a fine adjustment of the display of the TV monitor 31 is input using the keyboard 40, the command is input to the system controller 21. A signal corresponding to the command is transmitted to the TV monitor 31 from the system controller 21, so that fine adjustment, for example, control of illuminance of the display, is carried out.

Figure 2:
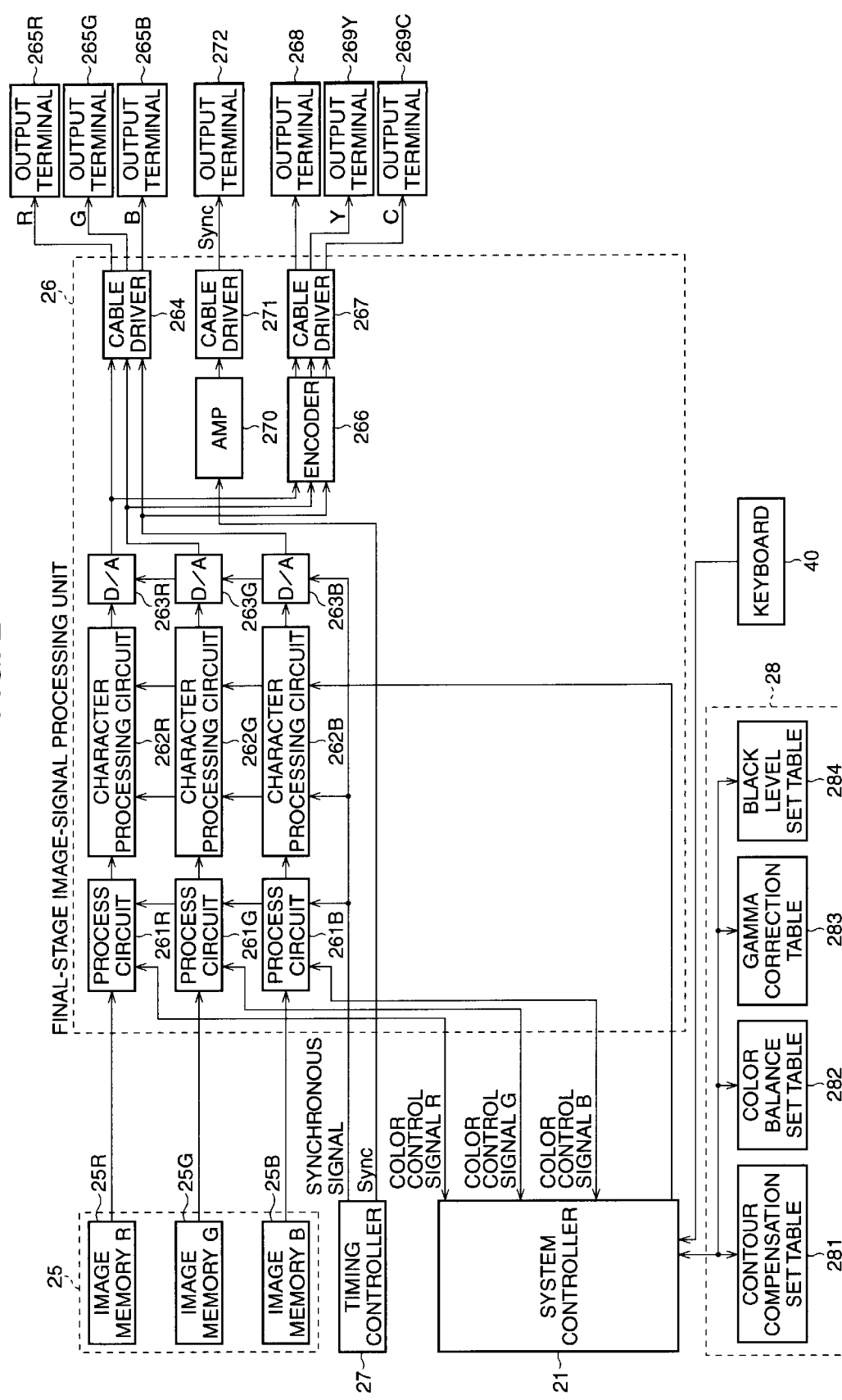
FIG. 2 is a block diagram showing a construction of a final-stage image-signal processing circuit and other elements connected to the final-stage image-signal processing circuit.

FIG. 2 is a block diagram showing a construction of the final-stage image-signal processing circuit 26 and other elements connected to the final-stage image-signal processing circuit 26. The image memory 25 includes image memories 25R, 25G and 25B. Image signals of R are stored in the image memory 25R, image signals of G are stored in the image memory 25G and image signals of B are stored in the image memory 25B. The image-signal processing database 28 includes a contour compensation set table 281, a color balance set table 282, a gamma correction table 283 and a black level set table 284.

Image signals read out from the image memories 25R, 25G, and 25B are respectively input to process circuits 261R, 261G, and 261B. On the other hand, with respect to the outputting device, a name of the model of the outputting device connected to the image-signal processing unit 20 is input to the system controller 21 using the keyboard 40. Note that, it will be explained next how to specify the model of the outputting device. Under the control of the system control 21, the above-mentioned tables of the database 28 are searched using the input a model name of the outputting device as a search key, and correction data for image signals, corresponding to the output characteristics of the outputting device, are obtained. Then, the correction data are output to the process circuits 261R, 261G and 261B, as color control signals R, G and B. In the process circuits 261R, 261G and 261B, signal operations are carried out in accordance with the output characteristics of the outputting device, based on the color control signals.

Then, in character processing circuits 262R, 262G, and 262B, character data, which are displayed with the reproduced image on the TV monitor 31, are superposed on the RGB digital pixel signals. Further, in D/A converters 263R, 263G, and 263B, the RGB digital pixel signals are respectively converted to RGB analog pixel signals.

The RGB analog pixel signals, output from the D/A converters 263R, 263G, and 263B, are output from output terminals 265R, 265G, and 265B, after passing through a cable driver 264.

Also, the RGB analog pixel signals, output from the D/A converters 263R, 263G, and 263B, are input to an encoder 266. In the encoder 266, a luminance signal (Y signal), a color signal (C signal), and a composite video signal of the NTSC (National Television System Committee) system are generated based on the RGB analog pixel signals. The composite video signal, the Y signal and the C signal are respectively output from output terminals 268, 269Y, and 269C, after passing through a cable driver 267.

In the first embodiment, the electronic endoscope system is provided with two sets of output terminals for each of the RGB analog signals, the composite video signal of the NTSC system, and the Y/C component signal. Note that, in FIG. 2, with respect to each of these signals, only one set of output terminal is depicted for clarity.

The synchronous signal, output from the timing controller 27, is amplified by the amplifier 270 and is output from an output terminal 272, after passing through a cable driver 271.

In the first embodiment, submenus or lists of the models of the outputting device shown in FIG. 3 are displayed on the display of the TV monitor 31. There is one submenu corresponding to each of the output terminals allocated at the rear of the image-signal processing unit 20. The submenu with the title "RGB output 1 set" is a submenu for selecting a device connected to the output terminals of the RGB analog video signals. The submenu with the title "S-Video output 1 set" is a submenu for selecting a device connected to the output terminal of the NTSC composite video signal. The submenu with the title "Y/C output 1 set" is a submenu for selecting a device connected to the output terminals of the Y/C component signals.

As shown in each of the submenus, three models of the outputting devices (represented by the letters A, B, C), for each type of a TV monitor, printer and VCR (Video Cassette Recorder), can be connected to the electronic endoscope system of the first embodiment. In each of the submenus, "★" indicates that the item which is at the right side is selected. The operator selects the model name of the outputting device which is connected to the corresponding output terminal, by using the arrow keys of the keyboard 40 and positioning "★".

For example, in FIG. 3, the positioning of "★" indicates that the monitor B is connected to the output terminal of the RGB output 1, the printer A is connected to the output terminal of the S-Video output 1, and the VCR-C is connected to the output terminal of the Y/C output 1.

As described above, the image-signal processing unit 20 is provided with two sets of output terminal for each of the RGB analog signals, the composite video signal of the NTSC system, and the Y/C component signals. Accordingly, practically, two submenus are displayed on the display of the TV monitor 31, corresponding to each of the RGB analog video signals, the NTSC composite video signal, and the Y/C component signals. In other words, another set of submenus similar to the submenus shown in FIG. 3 is displayed on the display.

Next, the tables of the image-signal processing database 28 are explained. FIG. 4 shows some records of the contour compensation set table 281 which is referred to in order to obtain a compensation coefficient α used for the contour compensation in the above-mentioned process circuits 261R, 261G, and 261B. In the contour compensation, the processes as follows are performed: an original image signal is delayed for one pixel; a difference between the original image signal and the delayed image signal is calculated; the leading and trailing edges of the original image signal are amplified by multiplying the difference by the compensation coefficient α.

As shown in the second column from the left side, in the first embodiment, a standard value of the compensation coefficient α is set to "1", with respect to the digital pixel signal R, the digital pixel signal G and the digital pixel signal B. Similarly, the compensation coefficient α for the monitor A is set to "1" with respect to the digital pixel signals RGB. For the monitor B, the compensation coefficient α is set to "2" with respect to the digital pixel signal R, and the compensation coefficient a is set to "1" with respect to the digital pixel signals G and B. The compensation coefficient α for the monitor C is set to "0.5" with respect to the RGB digital pixel signals.

FIG. 5 shows some records of the color balance set table 282 which is referred to in order to obtain a compensation value used for adjustment of the color balance in the above-mentioned process circuits 261R, 261G and 261B. As apparent from FIG. 5, with respect to the monitor A, the adjustment of the color balance is not carried out. With respect to the monitor B, the level of the R component is raised by "2", the level of the G component is lowered by "1". With respect to the monitor C, the levels of the RGB components are lowered by "2".

Figure 7:
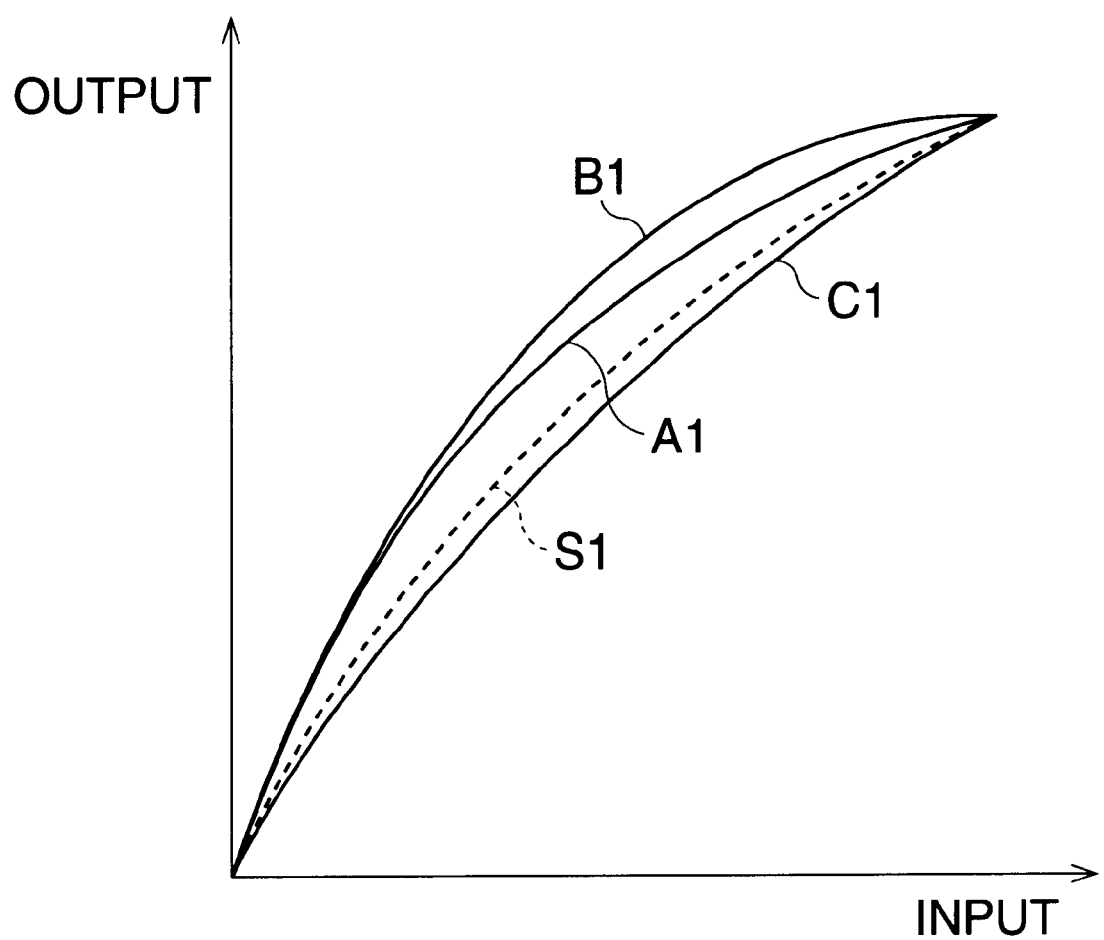
FIG. 7 is a graph showing gamma correction curves.

FIG. 6 shows some records of the gamma correction table 283 which is referred to when the gamma correction is carried out in the process circuits 261R, 261G, and 261B. As shown in FIG. 6, output levels are determined corresponding to each of input level. With respect to a standard gamma correction, output levels of the RGB components are set to the same level, shown in the second column form the left side. The output level corresponding to each input level is determined such that the corrected gamma curve has the characteristics of the broken line S1 of FIG. 7.

Similarly, with respect to the gamma correction of the monitors A and C, output levels of the RGB components are set to the same level. With respect to the monitor A, the output level corresponding to each input level is determined such that the corrected gamma curve has a characteristics of the line A1 of FIG. 7, and with respect to the monitor C, the output level corresponding to each input level is determined such that the corrected gamma curve has the characteristics of the line C1 of FIG. 7.

Further, with respect to the gamma correction in accordance with the characteristics of the monitor B. the output levels are shown from the fourth through the sixth columns from the left side. The output levels corresponding to each input level are determined in accordance with each of the RGB image signals, such that the corrected gamma curve of R or B has the characteristics of the line B1 of FIG. 7.

Figure 9:
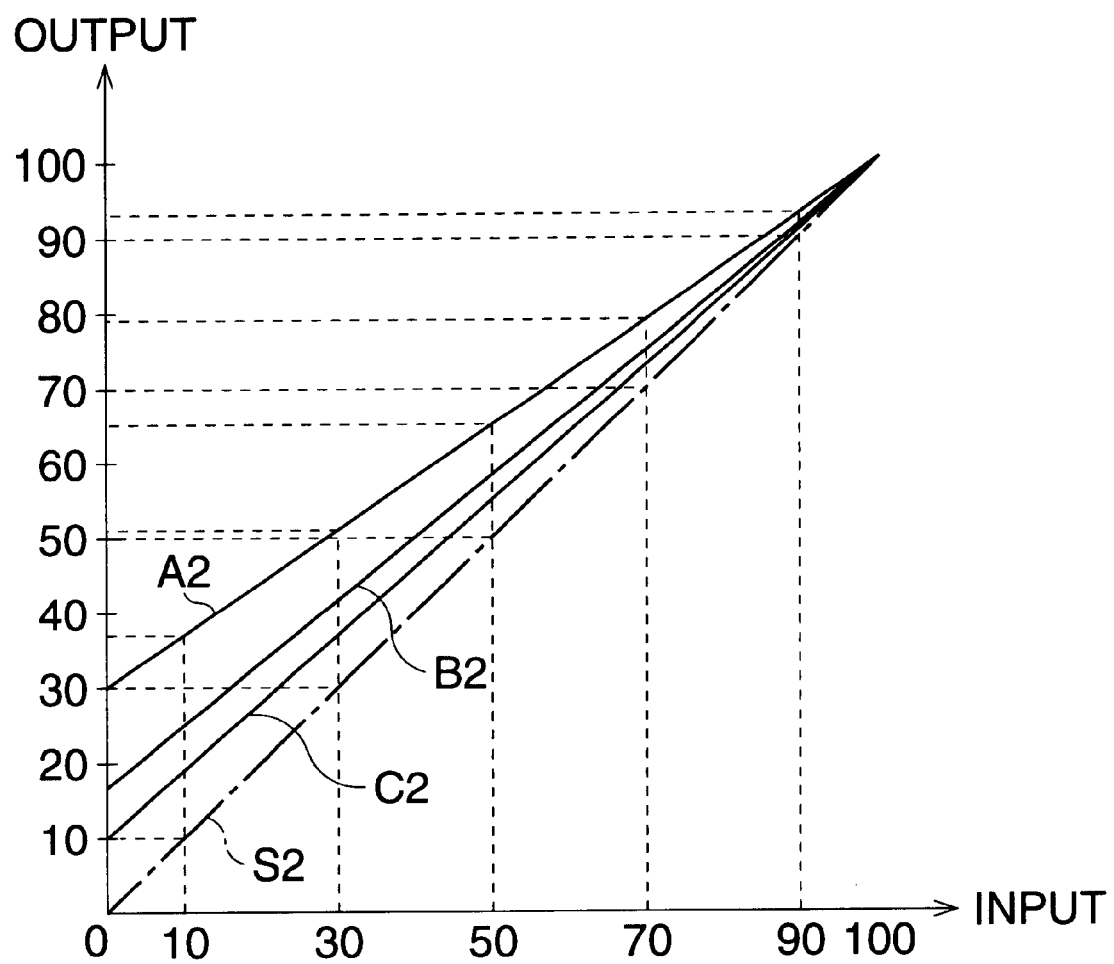
FIG. 9 is a graph showing the gain characteristics obtained by clamping the black level.

FIG. 8 shows some records of the black level set table 284 which is referred to when clamping the black level of the image signals. The clamping level is decided in the process circuits 261R, 261G, and 261B. Similar to the above-mentioned gamma correction table 283, output levels corresponding to each of the input levels are determined. With respect to the standard clamp level, output levels of the RGB component signals are set to the same level, shown in the second column form left side. All output levels are set to the same level as the corresponding input level, and the gain characteristics of the black level are indicated by line S2 in FIG. 9.

The clamp levels of the black level in the image signals output to the monitor A are shown in the third column from left side. When the input levels are "0", "10", "30", "50", "70" and "90", the clamp levels are respectively set to "30", "37", "51", "65", "79" and "93". The gain characteristics of the clamped black level are indicated by line A2 in FIG. 9.

Also, the clamp levels of the black level in the image signals output to the monitor B are shown in the fourth through sixth columns from the left side. With respect to the monitor B, the clamp levels corresponding to each input level, are determined in accordance with each of the RGB image signals, such that the gain characteristics of R are indicated by line B2 of FIG. 9.

The clamp levels of the black level in the image signals output to the monitor C are shown in the first column from the right side. With respect to the monitor C, the output levels of the RGB component signals are set to the same level, such that the gain characteristics are indicated by line C2 of FIG. 9.

Note that, in FIGS. 4, 5, 6 and 8, only the records for each type of monitor are shown. However, the above-mentioned tables will include records of each type of printer and VCR.

In the first embodiment, the image-signal processing database 28, including the tables 281 through 284, is stored in the ROM (Read Only Memory). If extra records of a new outputting device are added to the database 28, or some of the existing records are updated, a new ROM is installed in place of the old ROM by maintenance staff of the electronic endoscope system.

Figure 10:
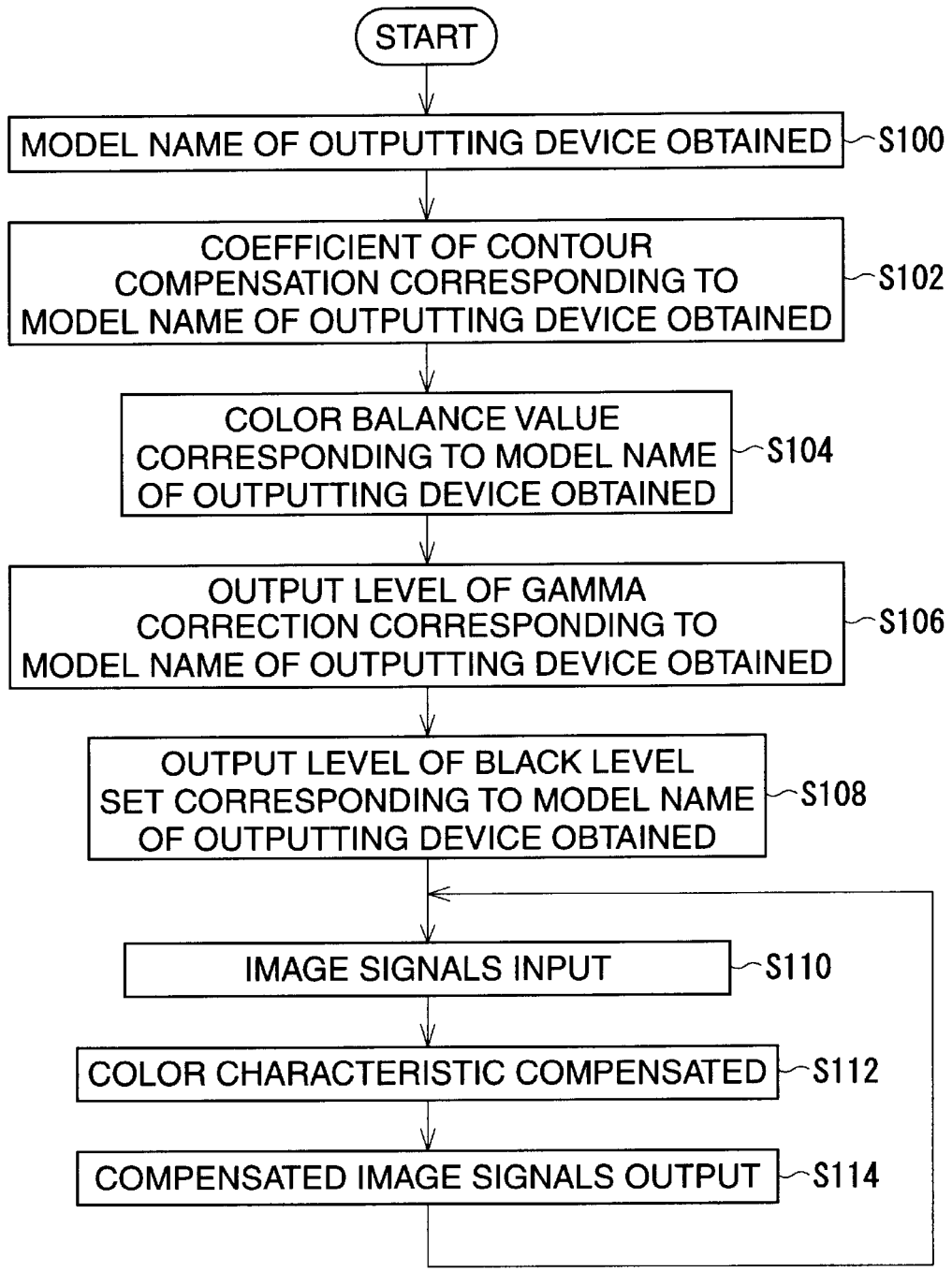
FIG. 10 is a flowchart showing a procedure for compensating image signals in the first embodiment.

FIG. 10 is a flowchart showing a procedure for correcting image signals in the first embodiment. The flowchart indicates the procedure for one output terminal.

In step S100, when the model name of the outputting device is specified by the keyboard 40 in the submenus of FIG. 3, the specified model name of the outputting device is input to the system controller 21. In step S102, the contour compensation set table 281 is searched using the specified model name of the outputting device as a search key. A value for the compensation coefficient α is obtained from a record matching the model name of the outputting device. In step S104, the color balance table 282 is similarly searched, a color balance value is obtained from a record matching the specified model name of the outputting device. In step S106, the gamma correction table 283 is similarly searched, and the output level is obtained from a record matching the specified model name of the outputting device. In step S108, the black level set table 284 is similarly searched, and the output level is obtained from a record matching the specified model name of the outputting device.

Namely, in step S102 through S108, each table of the image-signal processing database 28 is searched using the specified model name of the outputting device as the search key, and compensation data corresponding to the characteristics of the specified model name of the outputting device are obtained.

Then, after the image signals for one frame are input to the process circuits 261R, 261G, and 261B in step S110, the compensating processes are carried out in step S112, based on the compensation data obtained in step S S102 through S108. The RGB compensated image signals are respectively output to the D/A converters 263R, 263G, and 263B, to be converted to digital image signals, and the digital image signals are output from the output terminals to which the outputting devices are connected, in step S114. The operations from steps S110 through S114 are repeatedly carried out with respect to image signals for all frames.

The above-mentioned procedure is carried out with respect to each of the output terminals. Accordingly, the image signals which are compensated in accordance with the characteristics of the connected outputting devices are output from the corresponding output terminals.

As described above, according to the first embodiment, if a plurality of outputting devices which have different characteristics are connected to the image-signal processing unit 20, it is unnecessary for the operator to adjust the picture quality in accordance with each of the outputting devices.

Figure 11:
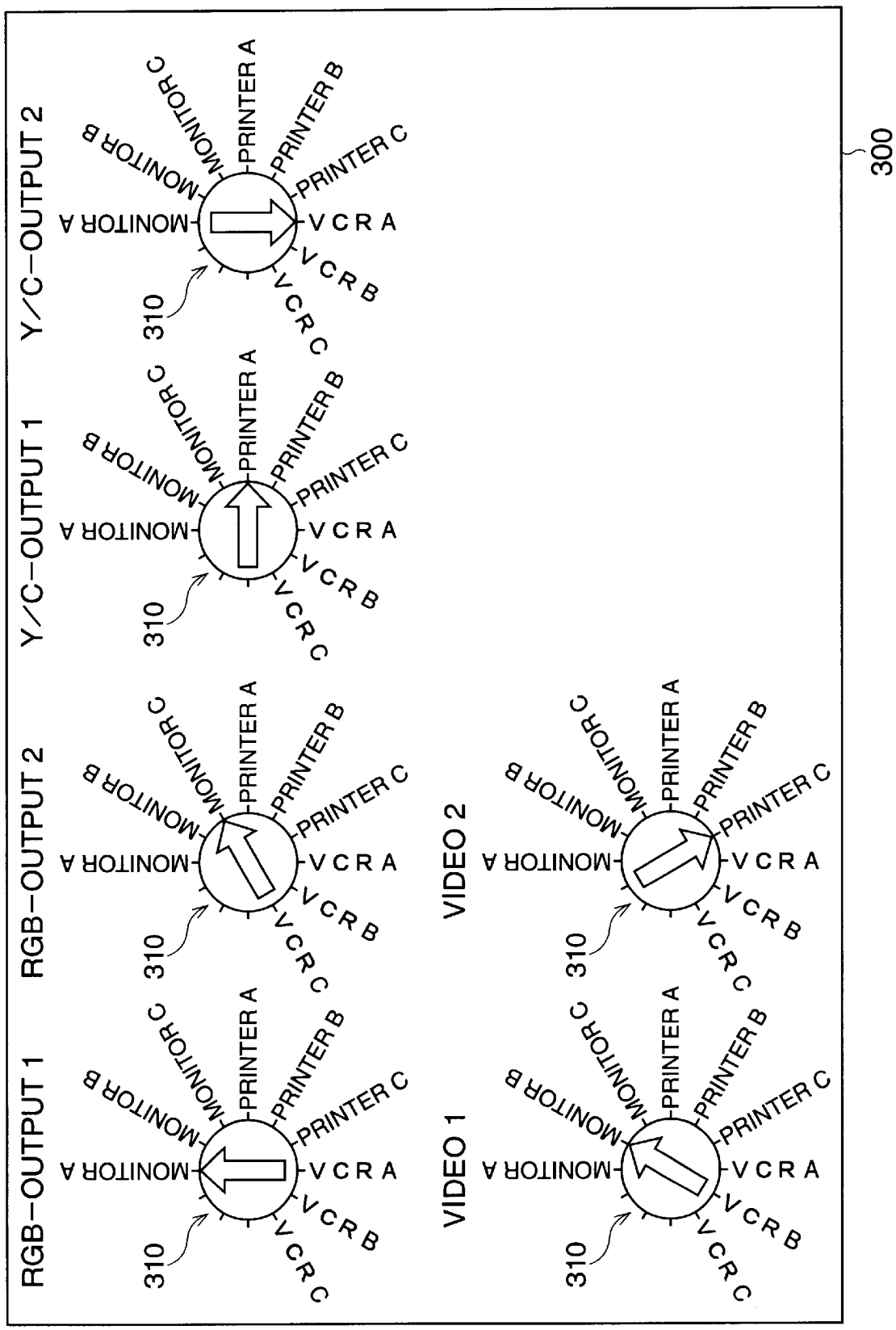
FIG. 11 is a front view of an outputting device selecting unit of an electronic endoscope system to which a second embodiment according to the present invention is applied.

FIG. 11 is a front view of an outputting device selecting unit 300 of an electronic endoscope system to which a second embodiment according to the present invention is applied. Note that, the construction of the electronic endoscope system of the second embodiment is similar to the construction shown in FIGS. 1 and 2. Further, in the second embodiment, the contents of the tables of the image-signal processing database 28 used for the compensation of the image signals are similar to the records shown in FIGS. 4, 5, 6, and 8.

The outputting device selecting unit 300 is provided on, for example, a back panel of the casing of the image-signal processing unit 20. The unit 300 has a plurality of rotary switches 310. In the second embodiment, the image-signal processing unit 20 is provided with two sets of output terminals, with respect to each of the RGB analog video signals, the Y/C component signals, and the NTSC composite video signal. One rotary switch 310 corresponds to one of the output terminals. The name of the corresponding output terminal is indicated above each of the rotary switches 310. All the output signals of the rotary switches 310 are input to the system controller 21.

Figure 12:
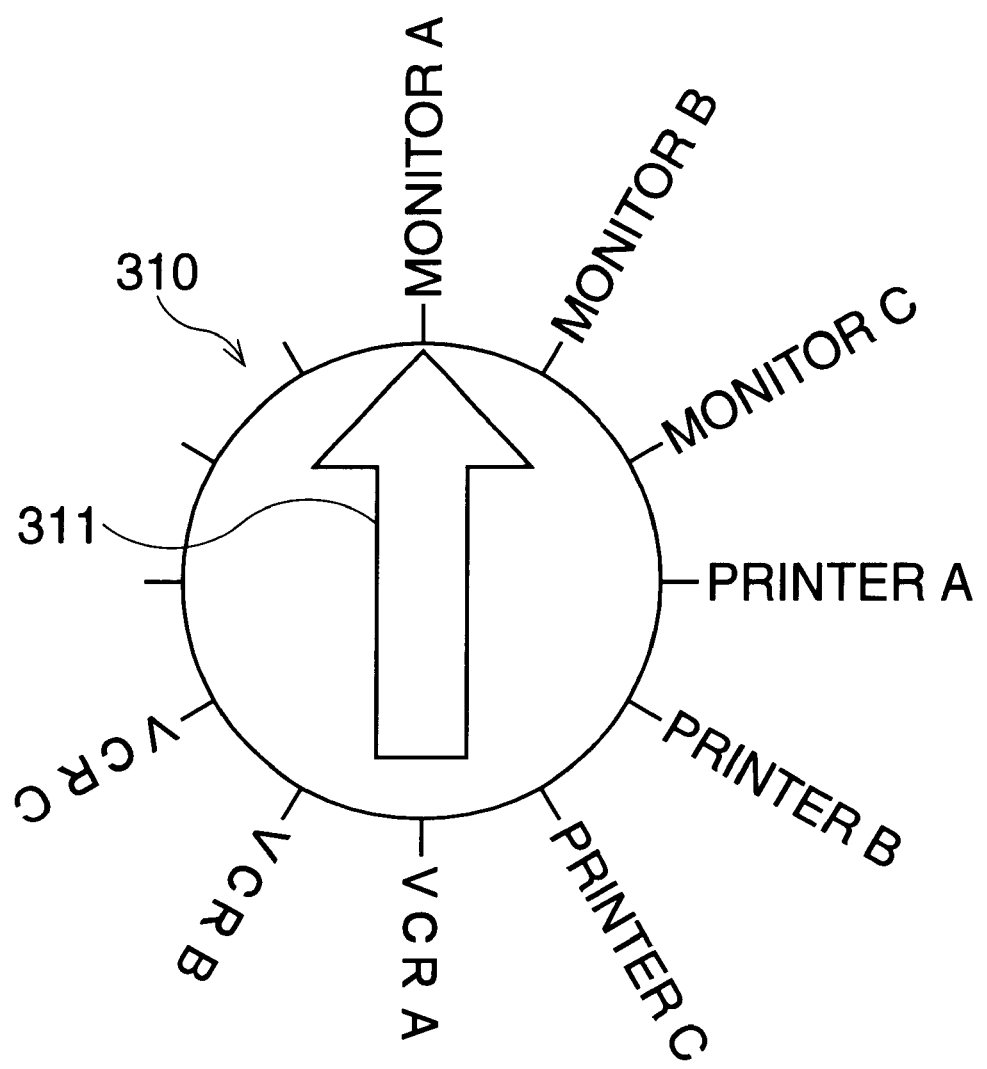
FIG. 12 is an enlarged view of a rotary switch of the outputting device selecting unit.

FIG. 12 is an enlarged view of the rotary switch 310. The model of the outputting device can be selected by rotating the knob 311 and positioning the tip of the arrow on the knob 311 at the name of the model of the outputting device. Similar to the submenus of the first embodiment, three models of the outputting device (A, B, and C), for a monitor, printer, and VCR, can be set.

The example shown in FIG. 11, indicates that the monitor A is connected to the output terminal 1 for the RGB analog video signals, the monitor C is connected to the output terminal 2 for the RGB analog video signals, the printer A is connected to the output terminal 1 for the Y/C component signals, the VCR A is connected to the output terminal 2 for the Y/C component signals, the monitor B is connected to the output terminal 1 (VIDEO 1) for the composite video signal, and the printer C is connected to the output terminal 2 (VIDEO 2) for the composite video signal.

As described above, when each of the rotary switches 310 is set in accordance with the model of the outputting device connected to the corresponding output terminal, the name of the specified model of the outputting device is input to the system controller 21 in step S100 in the flowchart of FIG. 10, and the above-mentioned operations are carried out.

Figure 13:
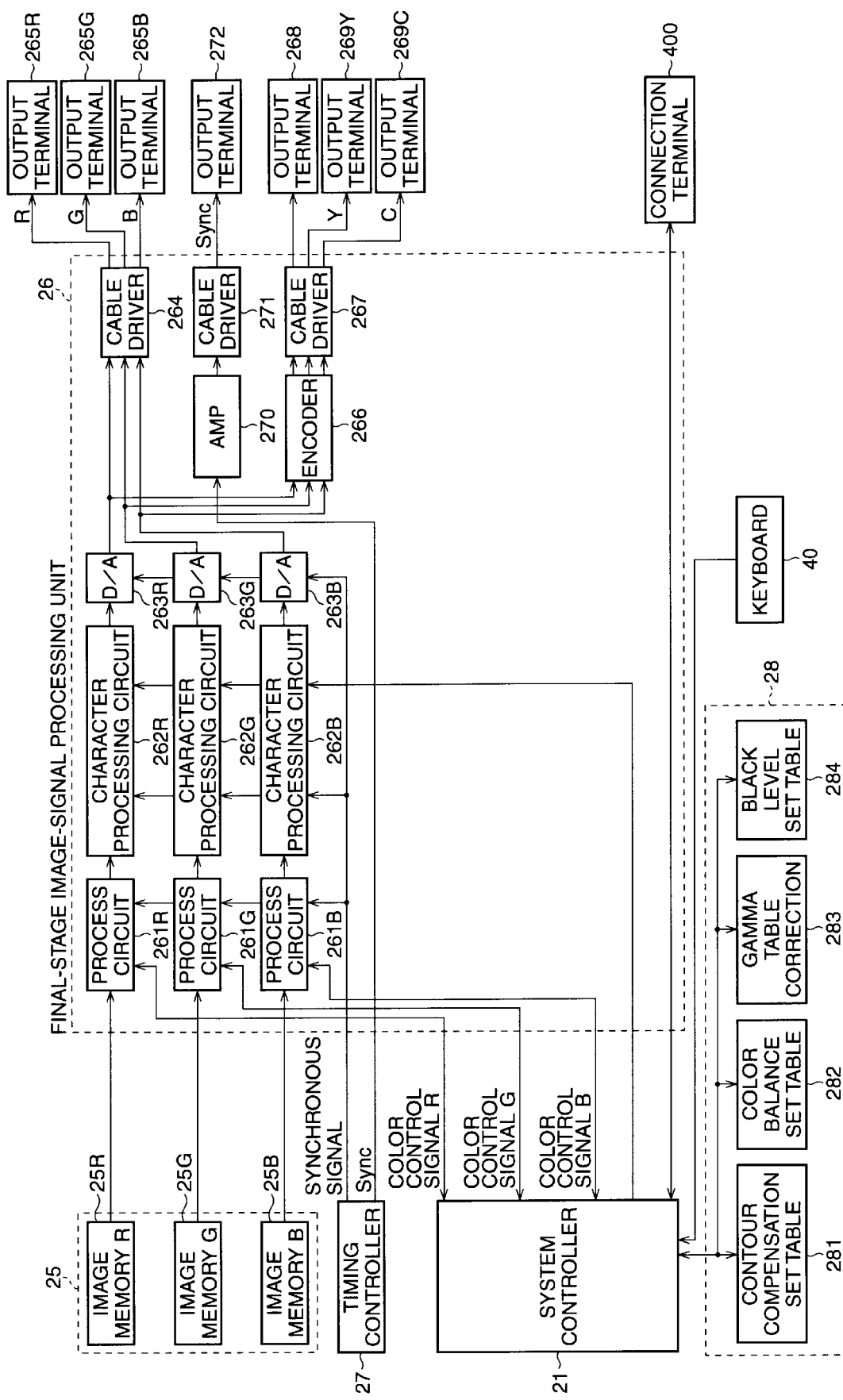
FIG. 13 is a block diagram showing a construction of a final-stage image-signal processing circuit and other elements connected to the final-stage image-signal processing circuit in an electronic endoscope system to which a third embodiment according to the present invention is applied.

FIG. 13 is a block diagram of the electronic endoscope system to which a third embodiment according to the present invention is applied. In FIG. 13, components utilized in the first embodiment, which are identical in the third embodiment, share the same reference numerals. The system controller 21 is provided with a connection terminal 400. Through the connection terminal 400, the system controller 21 can be connected to a LAN (Local Area Network) installed in a hospital where the electronic endoscope system is utilized.

In the third embodiment, the above-mentioned image-signal processing database 28 is stored in a storage unit (omitted in FIG. 13), for example, hard disk, in the image-signal processing unit 20. By accessing the system controller 21 through the connection terminal 400 from a remote terminal unit connected to the LAN, the database 28 can be maintained at remote places in the hospital. Further, if the LAN is connected to WAN (Wide Area Network), the database 28 can be accessed at remote places out of the hospital.

As described above, according to the present invention, the same picture quality can be obtained in images reproduced by different outputting devices having different characteristics.

The present disclosure relates to subject matter contained in Japanese Patent Application No. P2000-400694 (filed on Dec. 28, 2000) which is expressly incorporated herein, by reference, in its entirety.

What is claimed is:

1. An electronic endoscope system, provided with an image-signal processing unit that processes image signals obtained by a scope which is connected to said image-signal processing unit attachably and detachably, and at least one outputting device that is connected to said image-signal processing unit in order to output said image signals, said electronic endoscope system comprising:

an outputting device specifying tool that specifies the model of said at least one outputting device;

a database in which characteristic data concerning output characteristics of each model of said at least one outputting device are stored; and an image-signal compensator that obtains said characteristic data from said database based on the model specified by said outputting device specifying tool, and compensates said image signals using said obtained characteristic data, wherein said characteristic data are data concerning a picture quality of an image which is reproduced by said at least one outputting device, the image quality characteristic being directed to at least one of a compensation coefficient used for a contour correction process, a compensating value used for a color balance of said image signals, an output level value used for gamma correction of said image signals, and an output level value used for clamping a black level of said image signals.

2. An electronic endoscope system according to claim 1, wherein said image-signal processing unit comprises a plurality of output terminals to which said at least one outputting device can be connected, and the model of said at least one outputting device is specified by said outputting device specifying tool with respect to each of said output terminals.

3. An electronic endoscope system according to claim 2, wherein said outputting device specifying tool comprises:

a menu displayer that displays a list of models of said at least one outputting device, said list being displayed corresponding to each of said output terminals; and an input tool that selects one of the models corresponding to said at least one connected outputting device, from said list.

4. An electronic endoscope system according to claim 2, wherein said outputting device specifying tool is a rotary switch that is provided for each of said output terminals.

5. An electronic endoscope system according to claim 1, wherein said database is stored in a storage medium that is able to be replaced.

6. An electronic endoscope system according to claim 1, wherein said image-signal processing unit is able to be connected to an information communication network, and said database is able to be maintained by a remote terminal unit which is connected to said information communication network.

7. An electronic endoscope system according to claim 1, wherein said at least one outputting device is a monitor and a printer on which said image signals are reproduced.

8. An electronic endoscope system according to claim 1, wherein said characteristic data include the compensation coefficient used for the contour correction process.

9. An electronic endoscope system according to claim 1, wherein said characteristic data include the compensating value used for adjustment of the color balance of said image signals.

10. An electronic endoscope system according to claim 1, wherein said characteristic data includes the output level value used for gamma correction of said image signals.

11. An electronic endoscope system according to claim 1, wherein said characteristic data includes the output level value used for clamping the black level of said image signals.

12. An electronic endoscope system, provided with an image-signal processing unit that processes image signals obtained by a scope which is connected to said image-signal processing unit attachably and detachably, and at least one outputting device that is connected to said image-signal processing unit in order to output said image signals, said electronic endoscope system comprising:

means for specifying a model of said at least one outputting device;

a database in which characteristic data concerning output of each model of said at least one outputting device are stored; and means for obtaining said characteristic data from said database based on the model specified by said specifying means, and means for compensating said image signals by said obtained characteristic data, wherein said characteristic data are data concerning a picture quality of an image which is reproduced by said at least one outputting device, the image quality characteristic being directed to at least one of a compensation coefficient used for a contour correction process, a color balance of said image signals, an output level value used for gamma correction of said image signals, and an output level value used for clamping a black level of said image signals.

* * * * *